United States Patent [19]

Greenfield et al.

[11] Patent Number: 4,894,443

[45] Date of Patent: Jan. 16, 1990

[54] TOXIN CONJUGATES

[75] Inventors: Lawrence I. Greenfield, Albany, Calif.; Donald A. Kaplan, Midland, Mich.; Danute E. Nitecki, Berkeley, Calif.

[73] Assignee: Cetus Corporation, Emeryville, Calif.

[21] Appl. No.: 648,759

[22] Filed: Sep. 7, 1984

Related U.S. Application Data

[63] Continuation-in-part of Ser. No. 578,115, Feb. 8, 1984, abandoned.

[51] Int. Cl.$^4$ .................. A61K 39/00; A61K 39/02
[52] U.S. Cl. ..................... 530/388; 530/350; 530/387; 530/389; 530/390; 530/391; 530/820; 530/825; 424/85.91; 424/88; 424/92; 514/21; 514/2; 435/69.1; 435/69.7
[58] Field of Search .................. 424/85, 88, 85.91, 86, 424/92; 260/112 R, 112 B, 112.5 R; 530/385, 386, 387, 388, 390, 391, 820, 825, 350; 514/2, 6, 21; 435/68

[56] References Cited

U.S. PATENT DOCUMENTS

| | | | |
|---|---|---|---|
| 4,269,764 | 5/1981 | Patterson et al. | 260/112 R |
| 4,340,535 | 7/1982 | Voisin et al. | 260/112 B |
| 4,350,626 | 9/1982 | Masuho et al. | 260/112.5 R |
| 4,357,273 | 11/1982 | Masuho et al. | 260/112.5 R |
| 4,359,457 | 11/1982 | Neville, Jr. et al. | 424/85 |
| 4,363,758 | 12/1982 | Masuho et al. | 260/112 B |
| 4,368,149 | 1/1983 | Masuho et al. | 260/112 B |
| 4,379,145 | 4/1983 | Masuho et al. | 424/177 |

FOREIGN PATENT DOCUMENTS 0044167 6/1981 European Pat. Off. .

OTHER PUBLICATIONS

Trouet et al *Proc. Natl. Acad. Sci. U.S.A.* vol. 79, pp. 626–629, Jan. 1982 "A covalent linkage between daunorubicin and proteins: . . . in vivo studies".
Monsigny et al *FEBS Letters* vol. 119(1) Sep. 1980 pp. 181–186 "Preparation and biological properties of a covalent anti-tumor drug-arm-carrier (DAC) conjugate)".
Jelajaszewicz et al *Bacterial Toxins and Cell Membranes* 1978 Academic Press.
Ross et al *Eur J Biochem* vol 104, pp. 381–390 1980 "Increased toxicity of diptheria . . . 1980 F(ab')2 frament".
Hopp et al *Proc Natl Acad Sci* vol 78(6) pp. 3827–3828 Jun. 1981 "Prediction of Protein Antigenic Determinants from Amino Acid Sequences".
Margolin et al *Ann Rev. Viochem* 1970 vol. 39 1981.
Bacterial Toxins & Cell Membranes, Eds. Jelajaszewicz, J. and Wadstrom, T. (1978) Academic Press, pp. 291–332.
Pharmacology of Bacterial Toxins, Eds. Drews, J., and Dorner, F., Permagon Press Jansen, F. K., et al, Immun Rev (1982) 62:185–216.
Bacha, I., et al, J Biol Chem (1983) 238:1565–1570.
Bernhard, M. I., et al, Cancer Res (1983) 43:4420–4428.
Rowland, G. F., et al, Nature (1975) 255:487–488.
Arnon, R., et al, Immun Rev (1982) 62:1–27.
Moolten, F. L., et al, Immun Rev (1982) 62:47–72.

*Primary Examiner*—Robin L. Teskin
*Attorney, Agent, or Firm*—Kate H. Murashige; Gregory J. Giotta; Albert P. Halluin

[57] ABSTRACT

A novel class of polypeptides of the general formula $(F-(Pro)_n)_m F$, wherein F represents a flexible amino acid sequence wherein each amino acid is individually selected from the group consisting of serine, glycine, and threonine, and n is an integer from 4–8 inclusive and m is an integer from 1–4 inclusive, is disclosed. Thses polypeptides are useful in the construction of conjugates between antibodies and peptide toxins. The preparation of such conjugate toxins by linking antibodies to toxin/spacer composites prepared by recombinant techniques is also disclosed.

3 Claims, 4 Drawing Sheets

FIG. 1-1.

```
GAAAAGCTAAACAATACCTAGAAGAATTT CATCAAACGGCATTAGAGCATCCTGAATTG TCAGAACTTAAAACCGTTACTGGACCAAT CCTGTATTCGCTGGGCGTAACTATGGGGG
GluLysAlaLysGlnTyrLeuGluGluPhe HisGlnThrAlaLeuGluHisProGluLeu SerGluLeuLysThrValThrGlyThrAsn ProValPheAlaGlyAlaAsnTyrAlaAla
             250                              260                              270                              280

TGGCCAGTAAACGTTGCGCAAGTTATCGAT AGCGAAACAGCTGATAATTTGAAAAGACA ACTGCTGCTCTTTCGATACTTCCTGGTATC GGTAGCGTAATGGCATTGCAGACGGTGCC
TrpAlaValAsnValAlaGlnValIleAsp SerGluThrAlaAspAsnLeuGluLysThr ThrAlaAlaLeuSerIleLeuProGlyIle GlySerValMetGlyIleAlaAspGlyAla
             290                              300                              310                              320

GTTCACCACAATACAGAAGAGATAGTGGCA CAATCAATAGCTTTATCGTCTTTAATGGTT GCTCAAGCTATTCCATTGTAGGAGAGCTA GTTGATATTGGTTTCGCTGCATATAATTTT
ValHisHisAsnThrGluGluIleValAla GlnSerIleAlaLeuSerLeuMetVal    AlaGlnAlaIleProLeuValGlyGluLeu ValAspIleGlyPheAlaAlaTyrAsnPhe
             330                              340                              350                              360
                                                                      Msp I

GTAGAGAGTATTATCAATTATTTCAAGTA GTTCATAATTCGTATAATCGTCCCGCGTAT TCTCCGGGGCATAAACGCAACCATTTCTT CATGACGGGTATGCTGTCAGTGGAACACT
ValGluSerIleIleIleAsnTyrPheGlnVal ValHisAsnSerTyrAsnArgProAlaTyr SerProGlyHisLysThrGlnProPheLeu HisAspGlyTyrAlaValSerTrpAsnThr
             370                              380                              390                              400

GTTGAAGATTCGAATCCAAGACTGGTTTT CAAGGGAGAGTGGGCACGACATAAAAATT ACTGCTGAAAATACCCCGCTTCCAATCGCG GGTGTCCTACTACCGACTATTCCTGGAAAG
ValGluAspSerIleIleArgThrGlyPhe GlnGlyGluSerGlyHisAspIleLysIle ThrAlaGluAsnThrProLeuProIleAla GlyValLeuLeuProThrIleProGlyLys
             410                              420                              430                              440

CTGGACGTTAATAAGTCCAAGACTCATATT TCCGTAAATGTCGAAAATAAGGATGCGT TGCAGAGCTATAGACGGTGATGTAACTTTT TGTCGCCCTAAATCTCCTGTTTATGTTGGT
LeuAspValAsnLysSerLysThrHisIle SerValAsnValArgLysIleArgMetArg CysArgAlaIleAspGlyAspValThrPhe CysArgProLysSerProValTyrValGly
             450                              460                              470                              480
                                                                                                        Mbo I

AATGGTGTGCATGGAATCTTCACGTGGCA TTTCACAGAAGCAGTCGGATTCCATAGGC TCTAATGAAATTTCGTCGGATTCCATAGGC GTTCTTGGGTACCAGAAAACAGTAGATCAC
AsnGlyValHisGlyIleLeuHisValAla PheHisArgSerSerGluLysIleHis    SerAsnGluIleSerSerAspSerIleGly ValLeuGlyTyrGlnLysThrValAspHis
             490                              500                              510                              520

ACCAAGGTTAATTCTAAGCTATCGCTATTT TTTGAAATCAAAAGCTGAAGGTAGTGGGG TCGTGCCGG
ThrLysValAsnSerLysLeuSerLeuPhe PheGluIleLysSerTer
             530                                                              Msp I
```

FIG. 1-2.

FIG_2_

TOXIN CONJUGATES

CROSS-REFERENCE TO RELATED APPLICATION

This application is a continuation-in-part of copending U.S. patent application Ser. No. 578,115 filed 8 Feb. 1984 now abandoned.

DESCRIPTION

1. Technical Field

The present invention concerns the fields of cytotoxins, biochemistry, genetic engineering, and medicine. More particularly it concerns novel toxin conjugates, and components and uses thereof.

2. Background Art

Bacterial and plant toxins, such as diphtheria toxin (DT), *Pseudomonas a.* toxin A, abrin, ricin, mistletoe, modeccin, and Shigella toxin, are potent cytocides due to their ability to disrupt a critical cellular function. For instance, DT and ricin inhibit cellular protein synthesis by inactivation of elongation factor-2 and inactivation of ribosomal 60s subunits, respectively. *Bacterial Toxins and Cell Membranes*, Eds. Jelajaszewicz, J. and Wadstrom, T. (1978) Academic Press, p. 291. These toxins are extremely potent because they are enzymes and act catalytically rather than stoichiometrically. The molecules of these toxins are composed of an enzymatically active polypeptide chain or fragment, commonly called an "A" chain or fragment, linked to one or more polypeptide chains or fragments, commonly called "B" chains or fragments, that bind the molecule to the cell surface and enable the A chain to reach its site of action, eg, the cytosol, and carry out its disruptive function. The act of gaining access to the cytosol is called variously "internatlization", "intoxication", or "translocation". It is believed that the A chain must be timely liberated from the B chain—frequently by reduction of a disulfide bond—in order to make the A chain functional. These natural toxins are generally not selective for a given cell or tissue type because their B chains recognize and bind to receptors that are present on a variety of cells.

Derivatives of these bacterial and plant toxins have been prepared as therapeutic agents, primarily as antineopolastic agents, that are made specific for tumor cells or other target cells by replacing the native B chain(s) of the toxin molecule with a surrogate B chain that is specific for the tumor cell or adding a B chain having such specificity to the toxin molecule. *Pharmacology of Bacterial Toxins*, Eds. Drews, J. and Dorner, F. Pergamon Press. Synthetic cytotoxins containing the active fragment of a bacterial or plant toxin or a cytotoxic drug are called variously "chimeric toxins", "toxin conjugates", "cytotoxic conjugates", "hybrid toxins" or, when the surrogate B moiety is an antibody, "immunotoxins". Antibodies (polyclonal, monoclonal, and antigen binding fragments), hormones, lectins and various other compounds that are recognized by receptors on tumor cell surfaces have been used as surrogate B moieties. See European patent application publication No. 0044167, and U.S. Pat. Nos. 4,340,535, 4,350,626, 4,357,273, 4,359,457, 4,363,758, 4,368,149, and 4,379,145.

Surrogate B moieties have been chemically linked to toxin A chains by a variety of coupling agents. Heterobifunctional agents that include a disulfide group have been used extensively. The most popular of these agents is N-succidimidyl-3-(2-pyridyldithio)propionate (SPDP). *Immun Rev,* 62: 185–216 (1982) reports using a longer disulfide-containing coupling agent, 7-aza-8-oxo-10-(2-pyridyldithio)decanoic acid, to investigate whether greater separation between the A chain and antibody would increase activity. Increased activity was observed in an acellular system but not on intact cells, and the report concluded that the longer disulfide containing linker was not advantageous. Replacement of the disulfide bridge by a stable thioether bridge using a derivative of 6-maleimidocaproic acid as a bifunctional coupling agent for an A-antibody conjugate caused a 99% loss of activity relative to the disulfide conjugate in an intact cellular system.

The toxicity of diphtheria toxin for human lymphoblastoid cells was increased by covalent linkage to anti-lymphoblastoid (anti-CLA 4 and anti-Daudi) globulin. (Ross, W. C. J., et al, *Eur J Biodiem* (1980) 104: 381). Thyrotropin releasing hormone derivatives have also been conjugated to DT fragments such as CRM 45 to study the translocation function (Bacha, D., et al, *J Biol Chem* (1983) 238: 1565). DT-A conjugated using SPDP to a monoclonal antibody against guinea pig hepatocarcinoma cells showed specific cytotoxicity in vitro and in vivo (Bernhard, M. I. et al, *Cancer Res* (1983) 43: 4420).

Dextran, polyglutamic acid, and oligopeptides contaning up to four amino acid residues have been used as spacer arm bridges between cytotoxic drugs and antibodies. *Nature* (1975) 255: 487–488, *FEBS letters* (1980) 119: 181–186, *PNAS* (1982) 79: 626–629, and *Immun Rev,* 62: 1–27 (1982). These conjugates were reported to have higher toxicity in vitro than drug coupled directly to antibody.

Moolten, F. L., et al, *Immun Rev.* (1982) 62: 47–72 conclude that A chain-antibody conjugates may be more specific than native toxins, but lack much of the potency of the native toxin. They speculate that the loss of efficacy is because the internalization function is present in native B chains and surrogate B chains are inefficient substitutes as regards internalization. Use of toxins that lack a binding function but are otherwise intact, such as the (cross reacting mutant) CRM45 of DT or toxins whose binding function is chemically or enzymatically abrogated, are suggested, but no evidence of increased efficacy is given.

In summation, the efficacy of prior toxin-antibody conjugates has been highly variable due, inter alia, to variations in immunogenicity, target cell specificity, nonspecific toxicity, serum stability, effective concentration at the target cell, binding efficiency, and internalization efficiency. In this regard the main objects of the present invention are to provide (1) means for improving the efficacy of toxin-antibody conjugates and (2) novel toxin conjugates that include those means. The present invention provides an A-surrogate B geometry which permits more facile translocation of the A portion into the target cell, and a more stable mode by which antibody can be linked to the A portion. This latter property prevents premature decompostion prior to translocation of the A portion into the target cell.

SUMMARY OF THE INVENTION

The present invention provides novel toxin conjugates which are peculiarly effective in recognizing target cells and in effecting their demise. It also includes certain components of these toxin conjugates. These conjugates comprise a cytotoxic component which is an enzymatically active portion of the molecule, capable of killing cells in which it is internalized, a specific binding moiety, typically an antibody or fragment of an antibody, which is capable of recognizing a specific antigenic determinant or target cell, and a spacer which provides the proper geometry between the cytotoxic component and the binding fragment. These conjugates represent an improved delivery system for naturally occuring or modified cytotoxins ("A chains") which in their natural environment are bound to a relatively nonspecific binding component "B chain" (which is generally not an antibody). The naturally occuring toxins also contain, within the A-B chain fusion, sequences which are capable of cleavage intracellularly, ie which effect cleavage once the cytotoxic component has migrated to within the target cell, but are stable prior to this entry, and a translocation region which permits the desired cytotoxic A chain to enter the target cell. This intracellular cleavage exposes and labilizes the link (typically disulfide) between the A and B chain.

In the conjugates of the present invention, the non-binding portion of the molecule is constructed so as to retain the foregoing desired cytotoxic, intracellularly cleavable/extracellularly stable, and translocation properties of the natural molecule in a geometry suitable for connecting to a "binding fragment" and permitting activity. Thus, typically, the conjugates of the invention include: antibody or fragment of an antibody which is covalently linked, preferably through a bifunctional linker to a non-binding entity. The non-binding entity is an amino acid sequence which contains, to serve as the cytotoxic component, an enzymatically active site, an intracellularly cleavable/extracellularly stable site and translocation sequence and, as an extension of this amino acid sequence, a further sequence which serves as a spacer between the cytotoxic component and the binding fragment to be linked.

The spacer confers the additional advantage of enhanced solubility in some instances where intermediates for desired immunotoxin may be sufficiently insoluble to interfere with their purification. By supplying a relatively more soluble portion, or by altering the conformation of the remainder of the molecule, the spacer thus permits more options in the selection of components and conjugation methods.

The invention, therefore, relates to these conjugates and to the novel components used for their construction. Both the spacer segment and the non-binding portion of the conjugate formed by fusion of the spacer with a cytotoxic component, ie an extended spacer containing the cytotoxic component are aspects of the invention.

Thus, in one aspect, the invention relates to novel polypeptides (the spacer) consisting essentially of at least one rigid amino acid sequence bracketed by two flexible amino sequences—ie components of the formula (flexi-rigid)$_n$flex, where "flex" represents the flexible sequence and "rigid" the rigid sequence. In a preferred embodiment "flex" is about 4 to 8 amino acids each individually selected from the group consisting of threonine, serine and glycine and "rigid" is 4–8 proline residues. Such novel polypeptides are useful as spacers for separating the cytotoxic component and the target cell binding component of a toxin conjugate.

In the alternative, the spacer may be described in functional terms and comprises an amino acid sequence that:
(a) is substantially stable in serum;
(b) is substantially nonhydrophobic so as not to affect adersely the water solubility of the toxin conjugate;
(c) is at least about 15 A long;
(d) has a substantially extended structure; and
(e) is sufficiently flexible to permit three dimensional movement of the cytotoxic component and the target cell binding component.

The spacer may also be a solubilization conferring sequence of amino acids, as set forth hereinbelow.

The foregoing spacer descriptions are not mutually exclusive, but are alternative characterizations of successful peptide sequences. The spacer may further contain a reactive amino acid residue proximate one of its termini so as to provide a conjugation site for the additional binding fragment.

Other aspects of the invention are fused polypeptides for use in making toxin conjugates comprising:
(a) a cytotoxic portion; and
(b) one of the above-described polypeptide spacers.

The invention also concerns the DNA sequences encoding the spacer of fused polypeptide (cytotoxic/spacer); expression vectors containing these DNA sequences, and cells transformed with these vectors.

Still another aspect of the invention is a toxin conjugate which comprises:
(a) a cytotoxic portion;
(b) a polypeptide spacer bound to the cytotoxic component; and
(c) a target cell binding moiety conjugated to the cytotoxic component via the polypeptide spacer.

(The "cytotoxic portion" includes a site for intracellular cleavage within a serum stable domain and an internalization facilitating domain.)

In summary, the invention is designed to provide a toxin conjugate which has the appropriate geometry for translocating the cytotoxic fragment into the target cell, the capacity to retain its binding fragment prior to such translocation, and/or the ability to solubilize the cytotoxic portion. In one aspect of the invention, the spacer is designed so as to permit the cytotoxic portion of the molecule ready access to the cell membrane. As the size of a typical antibody (binding) fragment is very much greater than that of most cytotoxic fragments, there is considerable steric hinderance of the access to the cell membrane by the cytotoxic portion imposed by the sheer bulk of the antibody or antibody fragments. Accordingly, the conjugate toxins of the invention have a geometry schematically represented in (a) rather than that given without the spacer (b).

(a)     (b)

In order to effect this translocation, the spacer needs to be sufficiently flexible to allow the A portion to reach the cell membrane, and sufficiently extended to permit it to have sufficient reach.

The performance of the conjugated toxin can also be improved by securing the binding portion tightly to the remainder of the molecule with respect to a serum environment. This is done in one preferred embodiment of the invention, by utilizing a linker between the antibody and spacer which employs bonds not readily cleaved by reducing agents or by hydrolysis under extracellular conditions. The cleavage of the A-chain analog (ie the enzymatically active site) from the other end of the spacer arm can be achieved by permitting the linkage at the A end of the spacer to be more readily cleavable. This can best be done by retaining a portion of the original B chain of the native toxin in linking the A portion to the spacer. In this manner, the normal extracellular-resistant/intracellular-cleavable configuration of the A-B chain pair is retained but with the loss of the binding capacity of the original B portion. Thus, the specific binding capability conferred by the antibody on the conjugate is not lost prior to intracellular incorporation of the cytotoxic fragment.

Since the binding portion confers specific recognition of certain target cells, the conjugated toxins are useful in killing specified undesirable cells within a subject. Thus, in two other aspects, the invention relates to pharmaceutical compositions containing effective amounts of these toxins and to methods of treatment employing them.

BRIEF DESCRIPTION OF THE DRAWINGS

FIG. 1 shows the base sequence for the DT gene along with the corresponding deduced amino acid sequence.

MODES FOR CARRYING OUT THE INVENTION

A. Definitions

Figure 2:
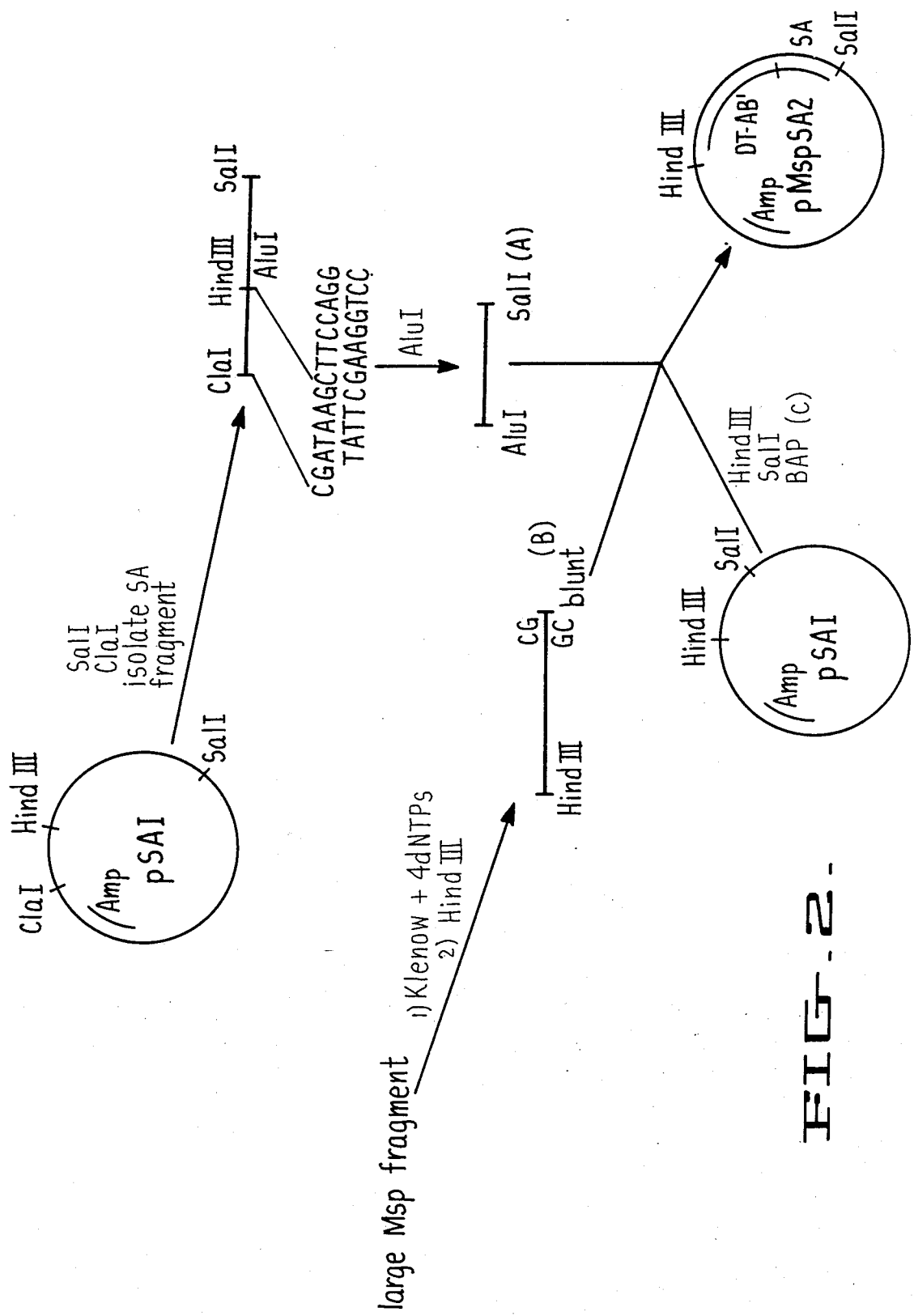
FIG. 2 shows the construction of an Msp-Spacer arm clone, pMspSA2.

As used herein the terms "fragment", "domain", and "region" and "portion" are interchangeable and refer to functionally but not necessarily physically distinct portions of the conjugated toxin molecule.

The term "specificity" as used to describe the target cell binding portion of the conjugated toxin means that the moiety has the ability to distinguish a target cell from other cells, typically due to the presence of a cell surface receptor that is unique to the target cells.

The term "selective" means that the cytotoxin has the ability to kill target cells preferentially, typically due to the specificity of the binding moiety or a differential in the respective quantities of receptors on target cells and other cells.

The term "target cells" means those cells which the cytotoxin is intended to kill. Although target cells will usually be tumor cells, they may be nontumorous cells whose selective destruction is desired for therapeutic or diagnostic purposes (for instance in certain assays of peripheral blood cells it is desired to selectively kill one or the other of B cells or T cells). The target cells may be present in living organisms or they may be preserved or maintained in vitro. The cells may be individual or associated to form an organ.

As used herein the term "polypeptide" or "protein" refers to an amino acid polymer. It is understood that such polymers exist in a variety of ionization states dependent on ambient pH, and that they may, further, be associated with accessory moieties—eg glycosylated, phosphorylated or conjugated to lipids. The peptides or proteins of the invention include all such forms, including unassociated forms.

The term "intracellular" is intended to include intracytoplasmic sites and sites within vesicular compartments such as lysosomes.

As used herein with respect to the enzymatically active polypeptide fragment the term "epitope" means a domain (amino acid sequence) of the fragment that is a causative factor in an immune response thereto.

"Target cell binding portion" refers to that fragment of the toxin conjugates of the invention which binds specifically to the target cells. In this invention the "binding" portion is an antibody or fragment thereof. The "non-binding" portion or fragment of the toxin conjugate comprises the remainder of the molecule. It thus includes the cytotoxin portion and the spacer.

The term "cytotoxic portion" includes the "enzymatically active polypeptide fragment" ie an A-fragment analogous sequence, the intracellularly cleavable/extracellularly stable domain and the translocation domain.

As used herein with respect to the construction of the spacer domain, "reactive amino acid residue" refers to an amino acid (or residue) which provides a site for linking or conjugation, as further set forth in B.4, below.

"Solubilizing conferring" sequence of amino acids in the context of the invention refers to a form of spacer sequence which continues at the (preferably C) terminus of the cytotoxic portion and which results in the fused protein being soluble in aqueous media, even when the cytotoxic portion is itself insoluble or when the cytotoxic portion would otherwise be rendered insoluble by the addition of a cysteine residue.

B. Structure of the Compounds of the Invention

Toxin conjugates have classically been conceptualized as combinations of an A fragment and a surrogate B moiety, attached through linking group that binds these fragments via a labile bridge such as a disulfide bridge. The rationale behind this conceptualization was that the function of the B moiety was primarily to bind the conjugate to the cell surface via interaction with a cell surface receptor and that the disulfide bridge provided means for joining the A fragment and B moiety that could be broken in vivo to liberate the A fragment. The present invention is based on an expanded conceptualization of the mode of operation of cytotoxic conjugates and takes into account factors including:

the spatial relationship between the cytotoxic moiety and the binding moiety, the role of the non-A portion of the conjugate in internalization, and the extracellular lability of the bond between the cytotoxic moiety and the binding moiety.

In the most preferred embodiment of the present invention with respect to toxin conjugates each of these factors is taken into account in synthesizing a novel toxin conjugate having five functional elements (which may overlap in the structure of the conjugate):

(1) an enzymatically active domain capable of the toxic activity of the A-fragment;

(2) an intracellular cleavage site within a extracellularly stable (or serum stable) domain that provides a site for liberating the enzymatically active domain from the remainder of the toxin conjugate after the toxin conjugate has been internalized;

(3) a translocation or internalization facilitating domain that acts as an adhesive to anchor the toxin conjugate molecule to the target cell membrane and/or to facilitate internalization;
(4) the novel polypeptide spacer described above; and
(5) a target cell binding moiety that recognizes and binds to a receptor on the target cell surface which by virtue of the receptor's quantity or nature causes the toxin conjugate to localize selectively on target cells relative to other cells.

In the most preferred embodiment the binding moiety is bound to the non-binding portion of the molecule (ie the remaining elements 1–4) by a chemical bond that is substantially resistant to cleavage in vivo (either extracellularly or intracellularly) thereby preserving the specificity of the molecule once it is administered, while the intracellular cleavage site within a serum stable domain is provided at the enzymatically active or "A" end of the spacer.

In order to effect this linkage using one preferred embodiment the cytotoxic portion of the toxin needs to be provided with a free cysteine residue, capable of forming a thio-ether linkage through a suitable bifunctional linker. The presence of this cysteine may interfere with the solubility of the toxic portion, and the spacer then serves the additional function of providing solubilization. To accomplish this purpose, the detailed "spatial" requirements relating to rigidity and flexibility of the sequence are not required; all that is needed are the hydrophilic or neutral solubility properties of the chain.

B.1. The Enzymatically Active Domain

The enzymatically active fragment of the conjugate may be the A chain of a bacterial or plant toxin or be a natural protein that has enzymatic activity similar to the A chain of a bacterial or plant toxin. As used herein the terms "enzymatically active fragment" and "A chain" are intended to include such similar acting natural proteins. Examples of such A chains are diphtheria A chain, exotoxin A chain (from *Pseudmonas aeruginosa*), ricin A chain, abrin A chain, modeccin A chain, alpha-sarcin, *Aleurites fordii* proteins, dianthin proteins, *Phytolacca americana* proteins (PAP I, PAP II, and PAP-S), momordin, curcin, crotin, gelonin, mitogellin, restrictocin, phenomycin, and enomycin.

The derivation of an A chain from a whole natural toxin molecule involves breaking the bond(s) between the A and B chain(s) (eg, reducing the disulfide bonds(s) between the A and B chain(s) with an appropriate reducing agent, such as 2-mercaptoethanol or dithiothreitol) and isolating the A chain from the B chain(s). The isolation may be carried out chromatographically or by other conventional protein fractionation techniques. The natural proteins that have enzymatic activity similar to the A chains of the natural protein toxins may be isolated from their sources, typically plant parts, by conventional protein extraction and isolation techniques. Following the isolation it may be possible depending upon the location and nature of the A chain epitopes and adjacent residues to remove one or more of the epitopes by partial proteolytic digestion or by chemical modification without affecting the enzymatic activity of the A chain. The enzymatically active fragment is perhaps most conveniently produced by cloning and expressing the gene encoding its amino acid sequence using the techniques of recombinant technology. When it is thus generated by genetic engineering, the epitopes may be removed at the DNA level by recombinant DNA techniques.

B.2. The Intracellular Cleavage Site

The intracellular cleavage site domain of the cytotoxin is preferably one that functions in a way that mimics the manner in which a natural toxin liberates its A chain. Three cleavage mechanisms are postulated currently: (1) proteolysis either enzymatic or chemical (eg, pH change), (2) disulfide reduction, and most commonly (3) a combination of (1) and (2). The cleavage site(s) of such domains is substantially stable extracellularly and is labile intracellularly. In the cleavage mechanisms involving proteolysis and disulfide reduction, extracellular stability is probably due to the position of the disulfide cleavage site in the extracellular tertiary structure of the conjugate. That is, the site is not exposed to cleavage agents in the extracellular environment, but is exposed in the intracellular environment due to a change in the tertiary structure of the molecule. Cleavage sites whose lability depends on pH are stable in extracellular environments, eg, blood, having a substantially neutral pH. The lower pH of certain intracellular compartments (eg, within a lysosome or receptosome) makes the site labile. The cleavage site domain comprises a sequence of amino acids that includes residues that are susceptible to proteolysis such as by lysosomal proteases. When disulfide reduction is involved the sequence will obviously contain a disulfide bridge formed by spaced cysteine residues. When both proteolysis and reduction are involved the A chain is liberated from the remainder of the toxin conjugate by proteolysis at the sensitive residues that causes a nick or break in the polypeptide backbone of the molecule and reduction of the disulfide bond. Examples of residues that are lysosomal protease sensitive are arginine, lysine, phenylalanine, tyrosine, and tryptophan.

In a preferred embodiment, this cleavage site in a serum stable domain is proximate the enzymatically active domain and forms an extension of the C-terminus thereof. Such a configuration can be provided most conveniently by providing an extended "A" fragment from a naturally occurring toxin into a portion of the natural B chain. Recombinant techniques are best suited to this embodiment, since convenient peptide cleavage techniques sepcific for the desired extension may not exist for a given toxin. However, the coding sequence can be cleaved and modified so as to encode for just the desired fragment.

B.3. The Translocation Domain

The internalization facilitating or "translocation" domain of the conjugate participates in interacting with the cell or vesicle wall whereby the wall is penetrated, opened, or disrupted to enable the conjugate to reach the intracellular compartment. The internalization facilitating domain may be identical to, or substantially similar in, amino acid content and sequence to an internalization facilitating domain of a bacterial or plant toxin or a polypeptide that is known to interact similarly with cell membranes. In the case of DT, the domain has been identified as being "hydrophobic" and located within the B fragment. The sequence of that segment possibly includes the following:

Val—Ala—Gln—Ala—Ile—Pro—Leu—Val—Gly—Glu—Leu
Val—Asp—Ile—Gly—Phe—Ala—Ala—Tyr—Asn—Phe—Val

Glu—Ser—Ile—Ile—Asn—Leu—Phe—Gln—Val—Val

Examples of polypeptides that are known to have a similar interaction with cell membranes are melittin:

Gly-Ile-Gly-Ala-Val-Leu-Lys-Val-Leu-Thr-Thr-
Gly-Leu-Pro-Ala-Leu-Ile-Ser-Trp-Ile-Lys-Arg-
Lys-Arg-Gln-Gln and delta lysine:

Met-Ala-Gln-Asp-Ile-Ile-Ser-Thr-Ile-Gly-Asp-Leu-
Val-Lys-Trp-Ile-Ile-Asp-Thr-Val-Asn-Lys-Phe-
Thr-Lys-Lys.

The position of the domain in the toxin conjugate molecule may vary. It will usually be located adjacent to the carboxy terminus of the A chain but may also be located adjacent to the amino terminus of the A chain. More than one internalization facilitating domain may be included in the conjugate if desired.

Since this domain is positioned adjacent the A chain, its inclusion in the toxin conjugate is most conveniently accomplished by recombinant DNA techniques. In DT, for example, the extension of the polypeptide sequence at the C terminus approximately 193 amino acids into the B chain provides such an internalization domain. Therefore, cloning and expression of the coding sequence for this portion of the DT toxin would provide the desired configuration. Alternatively, the oligonucleotides encoding known internalizing domains such as those exemplified above can be ligated to the nucleotides encoding the desired A fragment for cloning and expression.

B.4. The Spacer

The spacer comprises a sequence of amino acids that can be described in one of three non-mutually exclusive ways. In any case, the end of the spacer that attaches to the binding moiety may have a "reactive amino acid" residue at or near the terminus that provides a site for conjugating the binding moiety. For instance, if a reactive amino group at or near the end of the spacer is desired one or more lysine residues may be located near one terminus of the spacer fragment. If a reactive sulfhydryl group is desired, a cysteine residue may be situated similarly.

In one aspect, the spacer is described as having one or more extended structure portions (segments in which the peptide bond angles are enlarged) linked by segments that are flexible. Each end of the spacer terminates with a flexible segment. The spacer thus links the target cell binding moiety to the remainder of the molecule with the extended structure portion(s) serving to separate the binding moiety and the remainder of the molecule and the flexible segments permitting three dimensional movement of the binding moiety and the remainder of the molecule. Thus the spacer can be described as being formed from a series of extended structure portions in tandem with intermediate flexible regions (the flexible regions lie on either side of the extended structure regions), ie, has the general formula (flex-rigid)$_m$ flex. The extended (rigid) portion(s) of the spacer is preferably formed of a series of 4 to 8 prolines while the flexible portions are preferably composed of 4–8 amino acid residues each selected individually from the group consisting of serine, glycine, or threonine. The series of prolines form a left-handed proline II helix. These preferred spacers (less terminal reactive residue) may be represented by the formula $$(F-(Pro)_n)_m F$$

wherein F represents a flexible sequence composed of amino acids each selected independently from the group consisting of serine, glycine, or threonine, n is an integer form 4 to 8 inclusive, and m is an integer from 1 to 4 inclusive. The flexible sequences may be the same or different. A particularly preferred spacer domain (less terminal reactive residue) is defined by the sequence Gly-Thr-Gly-Ser-Gly-(Pro)$_n$-Ser-Gly-Ser-Gly-Thr where n is an integer from 4 to 8, inclusive, most preferably 6. A particularly preferred terminal reactive residue is cys.

In a second aspect, the spacer is substantially nonhydrophobic so that it has a neutral or positive effect on the water solubility of the conjugate. The spacer's hydrophobicity may be determined by summing the hydrophobicities of the individual amino acids (measured by partition coefficient tests) of which it is composed. A substantially nonhydrophobic sequence will measure neutral or hydrophilic. The hydrophilic nature of this segment will also place it on the surface of the configured molecule, thereby permitting accessibility for conjugation.

If the function of a particular spacer is merely to provide solubility during processing to a cytotoxic portion amino acid sequence, this property is, indeed, the only property required of it. Generally, the spacer is a relatively hydrophilic sequence, typically containing a cysteine residue.

In a third aspect, the spacer can also be described in functional terms as substantially stable in human serum, having a length selected such that it provides an extended structure link at least about 15 Å long, preferably about 30 to about 100 Å long, between the binding moiety and the remainder of the conjugate molecule, as being substantially non-hydrophobic so as not to adversely affect solubility, and having sufficient flexibility to permit three dimensional movement of the cytotoxic component with respect to the binding component.

B.5. The Target Cell Binding Moiety

The binding moiety may be any ligand that has the required target cell specificity. Antibodies, particularly monoclonal antibodies or their antigen binding fragments, are preferred binding moities. Monoclonal antibodies against surface receptors of target cells may be made by the somatic cell hybridization procedure first described by Kohler, G. and Milstein, C., *Nature*, (1975) 256: 495–497. The cell lines, reagents, and conditions used in this procedure are well known and have been reviewed extensively in the literature (*Somatic Cell Genetics*, (1979) 5: 957–972). Briefly the procedure involves immunizing a host with the immunogen of interest, collecting antibody-producing cells from the immunized host, fusing the antibody-producing cells from the immunized host with an appropriate tumor cell line using a fusogen such as polyethylene glycol, growing the cells in a selective medium to eliminate unhybridized partners, identifying hybridomas that produce antibody against the immunogen, growing such hybridomas, and collecting monoclonal antibodies from the resulting culture medium (for body fluid when grown in vivo). Antigen binding fragments (Fab, Fab', $F(ab')_2$, Fv) of the monoclonal antibodies may be made by digesting the whole Ig with an appropriate protease, for instance papain in the case of Fab and pepsin in the case of $F(ab')_2$. Antigen binding fragments will be particularly useful in instances where it is desired that the binding moiety lack its natural effector function. Antibodies of current interest will typically be of human, rat or murine origin since rat, mouse and human tumor cell lines are available for fusion. Also, a variety of antitumor monoclonal antibody reagents are rapidly becoming available. Human monoclonal antibodies are preferred for use in making conjugates for use in human therapy because of the reduced likelihood of immunogenicity.

C. Methods of Preparation

C.1 The Non-binding Portion (Cytotoxic-spacer Portions)

Depending on the sizes of the four polypeptide domains that make up the nonbinding portion of the conjugate toxins, these domains may be synthesized individually or as subunits by conventional polypeptide synthesis techniques (Margolin, A. and Merrifield, R. B., *Ann Rev Biochem,* (1970) 39: 841) and combined in sequence by known procedures.

Recombinant DNA methodology provides an alternative and preferred way of synthesizing the nonbinding portion of the conjugate, either as individual subunits, or as an entire fused polypeptide. This process involves obtaining a DNA sequence that encodes the nonbinding portion (or a particular domain or combination of domains) inserting the DNA sequence into a suitable expression vector, transforming microorganisms or cells with the vector, growing transformants that produce the desired fragment and harvesting the desired fragment from the transformants or their growth medium. The coding sequence may be made by synthesis of DNA subunits that encode portions of the enzymatically active fragment, translocation domain, cleavage site domain, and spacer domain and assembling them by ligation techniques known in the art, or by cloning those portions of naturally occuring genes which encode the desired protein. The DNA sequence that encodes the enzymatically active fragment will normally be isolated from naturally occurring DNA; as may the sequence encoding the cleavage and translocation domains. These and the spacer encoding sequence may also be made by conventional DNA synthesis techniques, and may be reproduced by conventional DNA cloning methods. Partial structural genes of bacterial or plant toxins that lack a binding function but retain their enzymatic, cleavage and internalization functions (eg, the CRM 45 mutant of DT) may be cloned and ligated to a DNA sequence that encodes the spacer. The ligation product is inserted into suitable expression hosts and expressed to make the nonbinding portion of the conjugate.

C.2. The Binding Portions

The binding portions of the conjugates of the invention are antibodies or fragments thereof. Use of monoclonal antibodies is preferred. Antibodies are prepared by means well known in the art, and can be isolated from serum, from spleen, or most preferably prepared and isolated from antibody secreting hybridomas. Many are commercially available (see B.5 herein).

C.3. Conjugation of Binding and Non-binding Portions

Since the antibodies or fragments thereof are prepared by reactions of immunoglobulins isolated from serum or from hydridomas, they must be linked in vitro to the non-binding domains. In a preferred configuration of the non-binding fragment, the cytotoxic portion of the molecule is extended from its C terminus by a sequence providing a spacer which has been provided with a reactive amino acid residue, cysteine, located at or near its C terminus. While bifunctional reagents, such as SPDP, that result in a labile disulfide (C-S-S-C) bridge between the spacer and binding moiety may be used as coupling agents, (and have often been so used where a cleavable link was desired) bifunctional reagents that form a stable (nonreducible) bond, such as a thioether (C-S-C) link are preferred. Such bonds are not susceptible to cleavage in the environment of use, that is, they are not cleaved extracellularly in vivo. Several protein coupling agents that form thioether bonds are available. These agents usually contain on one end of the molecule an activated carboxyl group that will react with free amino groups, eg. an ε-amino of a lysine of one of the conjugation partners (in this case the binding portion) and a maleimido or haloacetyl group that will react with a sulfhydryl of the other partner (in this case the non-binding portion) on the other end. Examples of such thioether-forming agents are active esters of the following acids: 6-maleimidocaproic acid, 2-bromoacetic acid, 2-iodoacetic acid, 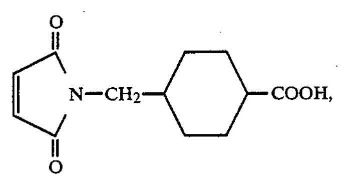 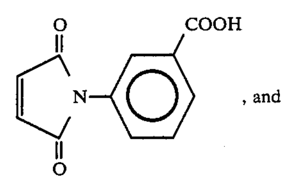 , and 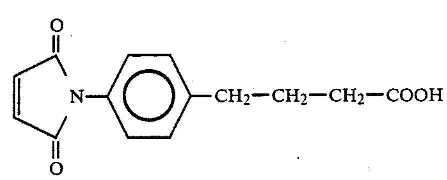 Activation of the carboxyl groups is required to permit reaction with amino groups of the chosen protein. The desired activated derivatives of the foregoing acids include most preferably the succinimidyl ester, ie although others, especially esters have been used, such as the water soluble ester formed from 1-hydroxy-2-nitro-4-sulfonic acid sodium salt, $$R-C(O)-O-\underset{NO_2}{\underset{|}{\bigcirc}}-SO_3Na.$$

Other coupling agents that may be used are various bifunctional derivatives of imidoesters such as dimethyl adipimidate.HCl, active esters such as disuccinimidyl suberate, aldehydes such as glutaraldehyde, bis-azido compounds such as bis(p-azidobenzoyl)hexanediamine, bis-diazonium derivatives such as bis-(p-diaoziumbenzoyl)-ethylene diamine, diisocyanates such as tolylene 2,6-diisocyanate, and bis-active fluorine compounds such as 1,5-difluoro-2,4-dinitrobenzene. Heterologous permutations of such bifunctional derivatives may also be used as well as peptide bond-generating reagents such as carbodiimides.

In a typical, preferred approach, a thioether linkage is formed between a sulfhydryl on the non-binding portion of the conjugate and the coupling agent and an amide linkage is formed between an ε-NH$_2$ of a lysine contained in the binding portion and the carboxyl of the coupling agent.

D. Mode of Administration

When used to kill target cells in vitro the conjugates will typically be added to the target cell culture medium in amounts ranging from about 1000 to about 100,000 conjugate molecules per target cell. The formulation and mode of administration for in vitro use are not critical. Aqueous formulations that are compatible with the culture or perfusion medium will normally be used.

When used in vivo for prophylaxis or therapy of humans or animals (eg, farm, laboratory, sport or pet animals) the cytotoxins are administered to the patient in a manner and dose that induce the desired target cell reduction response. They will normally be administered parenterally, preferably intravenously. The dose and dosage regimen will depend upon the nature of the target cell and its population, the characteristics of the particular cytotoxin, eg its therapeutic index, the patient, and the patient's history. The amount of cytotoxin administered will typically be in the range of about 0.01 to about 1 mg/kg of patient weight.

For parenteral administration the cytotoxins will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and Hank's solution. Nonaqueous vehicles such as fixed oils and ethyl oleate may also be used. Liposomes may be used as carriers. The vehicle may contain minor amounts of additives such as substances that enhance isotonicity and chemical stability, eg buffers and preservatives. The cytotoxin will typically be formulated in such vehicles at concentrations of about 1 mg/ml to 10 mg/ml.

E. Detailed Decription of a Preferred Embodiment

An illustrative and preferred embodiment of the invention comprises the components and intermediates in a specific conjugated toxin. In this toxin, the binding fragment consists of anti-Daudi antibodies which are linked by reaction with the succinimidyl ester of m-maleimidobenzoic acid to a spacer portion of the formula Gly—Thr—Gly—Ser—Gly(Pro)$_6$Ser—Gly—Ser—Gly—Thr—Cys
spacer                                                    reactive amino acid which is in turn a C terminal extension of a portion of the naturally occurring diphtheria toxin. Thus, the conjugate toxin here exemplified can be represented by the formula:

|DT—A| |DT—B'| |SPACER|—NHCHCH$_2$—S—[maleimide ring]—N—[phenyl]—C(O)—AB
                                                      COOH wherein DTA represents the enzymatically active portion, or "A" chain of diphtheria toxin, DT-B' represents the first approximately 190 amino acids of the diphtheria B chain, and AB represents the anti-Daudi antibody.

In this embodiment, three of the elements of the non-binding portion of the conjugate toxin are derived from diphtheria toxin; the enzymatically active domain, the cleavage site domain and the translocation domain. The mature diphtheria toxin molecule including both A and B chains contains 535 amino acid residues of which the A chain (the amino terminal fragment) contains 193 residues and the B chain (the carboxy terminal fragment) contains 342 residues. It appears that the intracellular cleavage site between the A and B chains in the native toxin is after one of the three Arg residues. Such cleavage readily takes place in vitro catalyzed by trypsin-like enzymes. It is thought that a similar cleavage takes place in vivo, thus exposing the disulfide link between the cysteine at position 186 and that at 201 for reductive intracellular cleavage. It is known that the amino terminal 193/342 of the B fragment contains sequences that cause the toxin to insert into artificial lipid bilayers under appropriate conditions forming ion conductive channels (Kagan, B. L., et al., *Proc. Natl Acad Sci* (USA), (1981) 78: 4950; Donovan, J. J., et al *Proc Natl Acad Sci,* (1972) 78: 172 (1972); Kaiser, G., et al *Biochem Biophys Res Commun,* (1981) 99: 358; *FEBS Letters* (1983) 160: 82). Thus the portions of the diphtheria toxin which are embodied in the illustrative conjugate toxin contain the intracellular cleavage/extracellularly stable connection between the A and B chain and at least a portion of the hydrophobic domain responsible for translocation of the cytotoxic portion into the cytosol.

FIG. 1 shows the sequence of the diphtheria toxin gene and the flanking regions, along with the deduced amino acid sequence. The deduced sequence is in reasonable agreement with the previously reported primary amino acid sequence data (Delange, R. J., et al, *Proc Natl Acad Sci* (USA) (1976) 73: 69; Delange, R. J., et al, *J Bio Chem* (1979) 254: 5827; Drazin, R. E., et al, (ibid) 5832 (1979); Delange, R. J., et al, (ibid) 5838 (1979); Falmagne, P., et al, Biochim Biophys Acta (1978) 535: 54; Falmagne, P., et al, *Toxicon* (1979) 17: supp 46; Lambotte, P., et al, *J Cell Biol* (1980) 87: 837; Capiau, C., et al, *Arch Phys* (1982) 90: B-96; Falmagne, P., et al, *Toxican* (1982) 20: 243). The deduced sequence assumes a leader sequence as shown, consistent with the fact that DTB is secreted from the natural source, *C. Diphtheriae* and with the fact that the sequence in this region strongly resembles known signal peptides (Michaelis, S., et al, *Ann Rev Microbiol* (1982) 36: 435). It is presently believed that the GTG codon at position $-25$ serves as a start codon and encodes methionine rather than the valine there shown.

The entire toxin gene sequence is carried by bacteriophage-$\beta$ and can be isolated from the phage by restriction with Xba 1 and EcoR 1. A shorter MspI fragment within this sequence (see FIG. 1) comprises most of the sequence used in the illustrative construct herein, this fragment results from MspI restriction about 300 bp preceding the first amino acid codon, and at the site shown at the codon encoding amino acid 382, approximately in the middle of the B fragment.

The construction of the illustrated conjugate toxin may be summarized as follows:

the Msp portion of the gene containing the codons for the A chain and approximately half of the B chain are ligated to synthetic DNA encoding the desired spacer with its reactive amino acid (cysteine) terminus. The resulting oligonucleotide is then modified to delete the promoter and ribosome binding regions as well as the codons for the leader sequence. It is then ligated into an operably linked position with respect to the $P_L$ promoter and N-gene ribosome binding site in suitable expression vector, along with an ATG start codon immediately preceding the glycine residue at position 1. Bacteria transformed with this expression vector produced the entire non-binding region of the molecule. The transformed cells are sonicated and the non-binding portion recovered from the sonicate. The non-binding portion is then linked to the anti-Daudi antibody in vitro using an activated m-maleimidobenzoic ester as linker.

E.1 Methods and Procedures

Construction of suitable vectors containing the desired coding and control sequence employs standard ligation and restriction techniques which are well understood in the art. Isolated plasmids, DNA sequences, or synthesized olignucleotides are cleaved, tailored, and religated in the form desired.

Cleavage is performed by treating with a suitable restriction enzyme (or enzymes) under conditions which are generally understood in the art, and the particulars of which are specified by the manufacturer of these commercially available restriction enzymes. In general, about 50 $\mu$g of plasmid or DNA sequence is cleaved by 50 units of enzyme in about 100 $\mu$l of buffer solution; in the examples herein, typically an excess of restriction enzyme is used to insure cleavage. Incubation times of about one hour to two hours at about 37° C. are workable, although variations can be tolerated. After each incubation, protein is removed by extraction with phenol/chloroform and the nucleic acid recovered from aqueous fractions by precipitation with ethanol followed by desalting over a Sephadex G-50 spin column. If desired, size separation of the cleaved fragments may be performed by polyacrylamide gel electrophoresis using standard techniques. A general description of size separations is found in *Methods in Enzymology* (1980) 65: 499–560.

Restriction cleaved fragments may be blunt ended by treating with *E. coli* DNA polymerase I (Klenow) in the presence of 0.01 mM of the four nucleotide triphosphates (dNTPs) using incubation times of about 15 to 25 min at 20° to 25° C. in 50 mM Tris pH 7.6, 50 mM NaCl, 6 mM $MgCl_2$ and 6 mM DTT. The Klenow fragment fills in at 5' sticky ends but chews back single strands even though the four dNTPs are present at 3' sticky ends. After treatment with Klenow, the mixture ie extracted with phenol/chloroform and ethanol precipitated and desalted by running over a Sephadex G-50 spin column. Treatment under appropriate conditions with S1 nuclease results in hydrolysis of any single stranded portion.

Synthetic oligonucleotides are prepared by the triester method of Matteucci, M., et al, *J. Am Chem Soc* (1981) 103: 3185. Kinasing of single strands prior to annealing or for labeling is achieved using approximately 10 units of kinase to 1–10 nmoles substrate in the presence of suitable buffers, ATP, $Mg^{+2}$, and EDTA (50 mM Tris, pH 7.6, 10 mM $MgCl_2$, 5 mM DDT 1–2 mM ATP, 0.1 mM spermidine, 0.1 mM EDTA, and 1.7 pmoles $\gamma^{32}$P-ATP 12.9 mCi).

Ligations are formed using approximately equimolar amounts of the desired components, suitably end tailored to provide correct matching, by treatment with about 0.4–1 Weiss units $T_4$ DNA ligase per $\mu$g vector DNA. Ligation mixtures are buffered at approximately pH 7.6 using 66 mM Tris along with 5 mM magnesium ion, 5 mM dithiothreitol, 1 mM ATP, 0.1 mg/ml BSA. For blunt ended ligation, 4–10 units of RNA ligase are added. Incubations are carried out at approximately 14°°C. overnight. The foregoing describes conditions suitable for ligation of blunt ends; sticky end conditions are conducted as above, but can be somewhat milder, employing a lower concentration of ligase and ATP, as is understood in the art.

In vector construction, the vector fragment is commonly treated with bacterial alkaline phosphatase (BAP) in order to remove the 5' phosphate and prevent self ligation of the vector. BAP digestions are conducted at pH 8 in approximately 150 mM Tris, in the presence of $Na^+$ and $Mg^{+2}$ using about 1 unit of BAP per $\mu$g of vector at 60° for about one hr. In order to recover the nucleic acid fragments, the preparation is extracted with phenol/chloroform and ethanol precipitated and desalted by application to a Sephadex G-50 spin column. Alternatively, the religation can be prevented by additional restriction of one of the fragments.

In the constructions set forth below, correct ligations for plasmid construction are confirmed by transforming *E. coli* strain MM294 (obtained fronm the *E. coli* Genetic Stock Center, CGSC#6135) with the ligation mixture, unless the $\lambda$ phage $P_L$ promoter is used; in this case *E. coli* strain MC1000 Lambda $SN_7N_{53}C_{I857}SusP_{80}$ is used (ATCC 39531 deposited Dec. 2, 1983.) This strain is hereinafter referred to as MC1000-39531. Successful transformants are selected by ampicillin, tetracycline or other antibiotic resistance or using other markers depending on the mode of plasmid construction as is understood in the art. Plasmids from the transformants are then prepared according to the method of Clewell, D. B., et al *Proc Natl Acad Sci* (1969) 62: 1159, following chloramphenicol amplification (Clewell, D. B., *J. Bacteriol* (1972) 110: 667) and analyzed by restriction and/or sequenced by the method of Messing, et al, *Nucleic Acids Res,* (1981) 9: 309 or by the method of Maxam, et al, *Methods in Enzymology* (1980) 65: 499.

Transformations were performed using the calcium chloride method described by Cohen, S. N., et al, *Proc Natl Acad Sci* (USA) (1972) 69: 2110.

Two host strains are used in cloning an expression of the plasmids set forth below:

For most constructions, *E. coli* strain MM294 (CGSC#6135), Talmadge, K., et al, *Gene* (1989) 12: 235; Meselson, M., et al, *Nature* (1986) 217: 1110 is used as the host. However, when expression is under control of the $P_L$ promoter the *E. coli* strain MC1000 Lambda $SN_7N_{53}C_{I857}SusP_{80}$ is used (ATCC 39531). This strain contains a lambda prophage which codes for a temperature sensitive $C_I$ repressor, which at the permissive temperature (30°–34° C.) is active. However, at the nonpermissive temperature (38°–48° C.), the repressor is inactive and transcription from the $P_L$ promoter can proceed. The $N_7$ and $N_{53}$ mutations prevent excision of the prophage from the chromosome and phage production is thus inhibited in this strain.

E.2 Isolation and Cloning of the MspI Fragment from the DT Gene

DNA was isolated from corynephage $\beta^{Tox+}$ grown on *Corynebacterum diphtheriae* $C7^{(-)tox-}$. (The host and phage are obtainable from J. Collier, University of California, Los Angeles; see Tweten, R. K., et al, *J Bacteriol* (1983) 156: 680.

To prepare DNA, high-titered β phage stocks were prepared in "TYE' medium" (15 g/l bactotryptone, 10 g/l yeast extract, 5 g/l NaCl supplemented with 1 mM $CaCl_2$), by the method of Holmes, R. K., et al *J Virology* (1969) 38: 586. Upon completion of lysis, debris was removed by centrifugation at 13,000×g for 5 min, and NaCl added to 0.5M, followed by PEG to 100 g/l, and the mixture was stirred overnight at 4° C. The phage were concentrated by centrifugation at 13,000×g for 15 min and resuspended in 100 mM Tris HCl pH 7.5, 100 mM NaCl, 20 mM EDTA. Pronase was added to 1 mg/ml and the mixture was incubated at 37° C. for 2 hr. After removal of PEG by addition of potassium phosphate (dibasic:monobasic/2:1) to 23% and centrifugation at 6,000×g for 5 min, the lower phase was extracted with phenol, ethanol precipitated and the DNA purified by banding in a CsCl-EtBr gradient.

Approximately 500 μg of the phage DNA (MW=22×10^6 daltons) was treated with EcoRI and XbaI and the resulting mixture run on 1.7 liters 1% agarose gel at 90 volts for 35 hr. The XbaI/EcoRI fragment (1.5×10^6 daltons) containing the toxin gene was cut out, run through a syringe, and electroeluted in 1/10 TBE for 4 hrs at 500 volts onto a spectropore dialysis membrane. The DNA was retreived from the membrane using 0.25% SDS in 1/10 TBE, phenol extracted, ether extracted, and ethanol precipitated.

The resulting DNA was further restricted with MspI, the DNA resolved on 5% PAGE, and the two MspI fragments isolated by the crush and soak method. The large Msp fraction (see FIG. 1) which contained control sequences, leader, A, and partial B sequences from the toxin was cloned by ligating approximately 5 ng of the fragment with 2 μg of ClaI-restricted, BAPed, pBR322. The ligation mixture was transformed into *E. coli* MM294, and the desired clones determined by isolation of plasmids, restriction analysis and sequencing. The desired cloning vector was designated pMsp. Although this cloning was accomplished as above, constructions to provide the non-binding portion were obtained using phage directly as the source of Msp fragment.

E.3. Synthesis and Cloning of Spacer Coding Sequence

A DNA fragment encoding the amino acid sequence

Gly-Thr-Gly-Ser-Gly-(Pro)$_6$-Ser-Gly-Ser-Gly-Thr-Cys and flanked by sequences defining convenient restriction sites and a stop codon was designed and synthesized by conventional DNA synthesis procedures.

The sequence,

```
AG CTT CCA GGC ACT GGA TCT GGC—
   Gly Thr Gly Ser Gly—
   CCG CCG CCA CCG CCG CCT TCT GGA TCC GGT ACC TGC TGA G
   Pro Pro Pro Pro Pro Pro Ser Gly Ser Gly Thr Cys Stop
``` and its complement were prepared using the triester method of Matteucci (supra) and annealed and kinased to give the double stranded sequence:

```
P—AGCTTCCAGGC---------ACCTGCTGAG
        AGGTCCG---------TGGACGACTCAGCT—P
   HindIII                            SalI
```

The annealed sequence was cloned as follows: pBR322 (25.72 μg) was restricted with SalI and HindIII, BAPed, phenol extracted and desalted over a one cc Sephadex G-50 column. The kinased annealed, double stranded spacer encoding sequence (0.2 pmoles) was ligated with 1 μg of the plasmid vector fragment, and the ligation mixture was used to transform *E. coli* strain MM294. $Amp^R Tet^S$ colonies were screened for plasmid size. The desired plasmid, pSA1 was confirmed by restriction analysis and sequencing.

E.4. Cloning of Spacer onto Msp1 Fragment

The plasmid, pMspSA2 which contains the MspI fragment coding sequence ligated to the spacer coding sequence was constructed as outlined in FIG. 2.

pSA1 plasmid DNA (77 μg) was restricted with SalI and ClaI, run on a 12% polyacrylamide gel and the fragment containing the spacer arm sequence isolated by the crush and soak method. One half the sample was further restricted with AluI to give "fragment A". As shown in FIG. 2, the Alu cleavage results in a blunt end 6 bp upstream from the glycine codon.

The large MspI fragment (10 ng) isolated from phage as in E.2 was blunt ended by filling in with Klenow fragment and dNTPs. The mixture was run over a Sephadex G-50 column, treated with HindIII, and re run over a 1 cc Sephadex G-50 column to give "fragment B". As seen from FIG. 1, HindIII restriction deletes a portion of the DT control sequences, but probably leaves at least a portion of the promoter and ribosome binding site, and the entire leader sequence.

For the vector, 77 μg pSA1 was restricted with HindIII and SalI, treated with BAP, and the vector DNA fragment purified with a 1 cc Sephadex G-50 column to give "fragment C".

The ligation mixture consisted of 4 μg of fragment C, 3 ng of fragment B, and 20 ng of fragment A under standard ligation conditions. Following ligation overnight at 12° C., the mixture was transformed into *E. coli* strain MM294, and $Amp^R Tet^S$ colonies screened for plasmid size. The desired construct was identified by restriction analysis and confirmed by Maxam-Gilbert sequencing. This plasmid, pMspSA2 contains, between the HindIII and SalI sites of pBR322, a portion of the DT control sequence, leader sequence, A fragment, B fragment through the codon for amino acid 382, and the spacer arm codons.

E.5. Deletion of the DT Promoter and Leader Sequences

Figure 3:
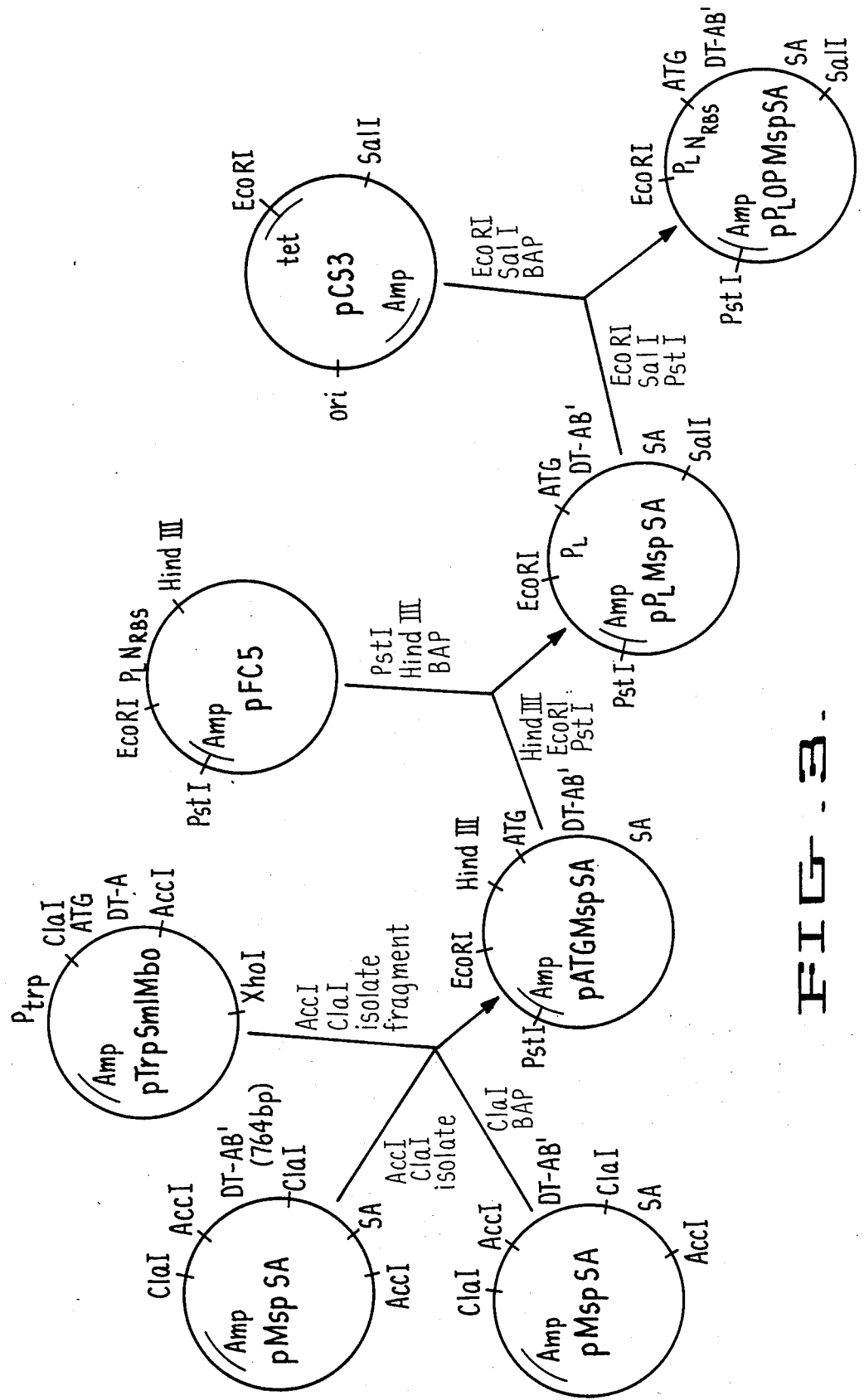
FIG. 3 shows the construction of two Msp-Spacer fragment expression vectors wherein the coding sequence is under the control of the $P_L$ promoter: $pP_L$MspSA and $pP_L$OPMspSA2.
Figure 4:
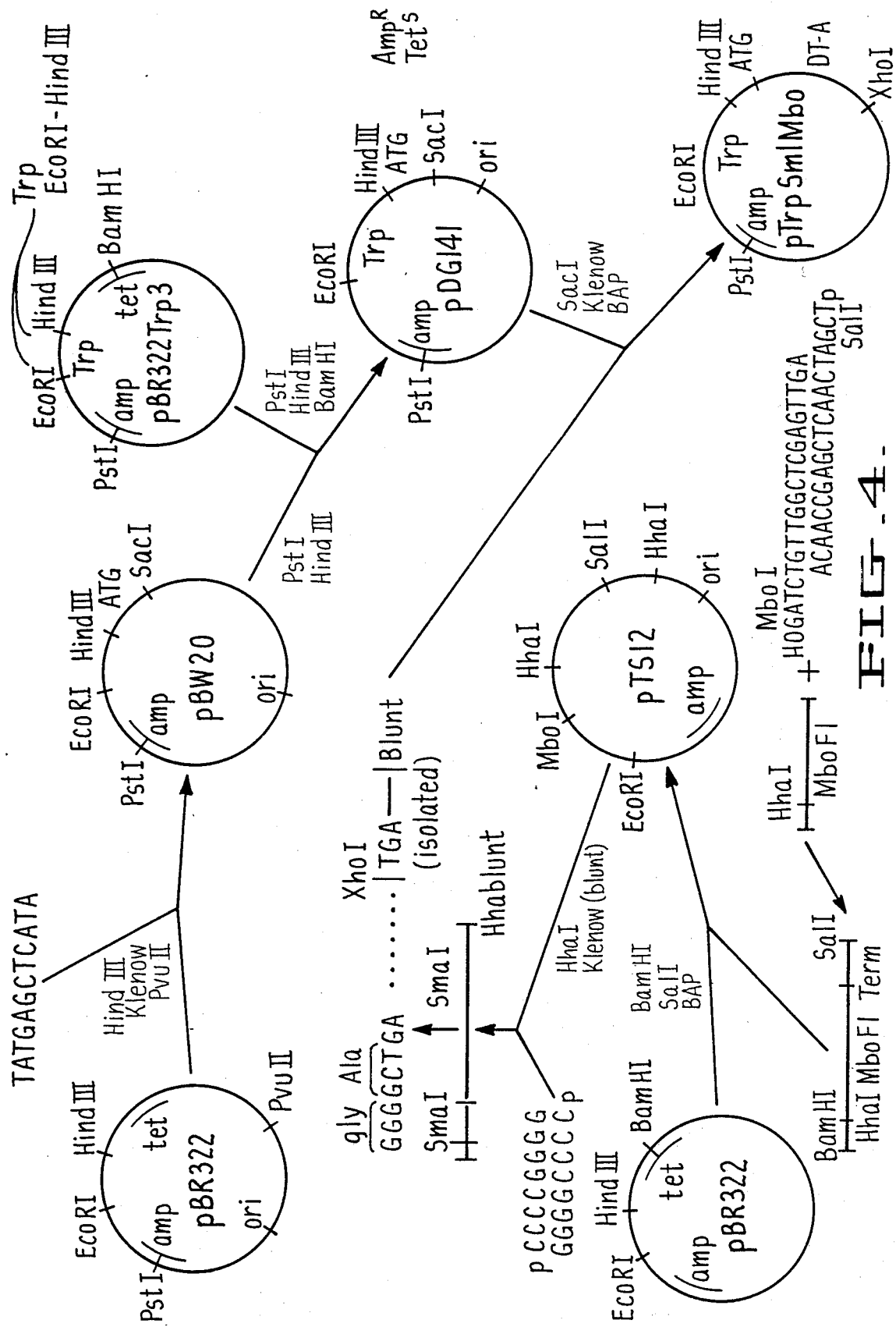
FIG. 4 shows the construction of pTrpSmlMbo.

The preparation of pATGMspSA is outlined in FIG. 3.

pTrpSmlMbo (55 μg) was double digested with AccI and ClaI and the short fragment spanning the ATG start codon and a portion of the A fragment isolated. (See FIG. 4 for relevant sequences in pTrpSmlMbo and paragraph E.10 for its construction.)

A vector fragment was prepared by digesting 25 μg of pMspSA with ClaI, and treating with BAP. The missing portions of the Msp toxin fragment were supplied by a digest of 50 μg of pMspSA with AccI and ClaI and isolating the 764 bp fragment between these sites in the coding sequence.

A ligation mixture containing 250 ng of the ATG-partial A fragment from pTrpSmlMbo, 700 ng of the partial A-partial B fragment from pMspSA and 2 μg of the spacer-vector fragment from pMspSA was transformed into *E. coli* MM294 and $Amp^R Tet^S$ colonies selected. The correct construction was confirmed by restriction analysis.

E.6. Preparation of Expression Vectors pP$_L$MspSA and pP$_L$OPMspSA and Expression of the Toxin-Spacer Construct One expression vector, pP$_L$MspSA was constructed by inserting the appropriate portions of pATGMspSA behind the P$_L$ promoter. The construction is shown in FIG. 3. pATGMspSA was digested with HindIII, PstI, (EcoRI to prevent religation) and the large vector fragment containing the ATG start codon, the A and B' DT toxin and spacer coding sequences used in subsequent ligation. This fragment was then ligated with a PstI, HindIII, BAPed preparation of pFC5 (see parag. E.9, below) which fragment corresponds to the portion of pFC5 containing the P$_L$ promoter and N-gene ribosome binding site. The ligation mixture was then used to transform MC1000-39351 and transformants selected by Amp$^R$. The correct construction of the desired plasmid pP$_L$MspSA was confirmed by restriction analysis.

A second vector, pP$_L$OPMspSA was constructed by a two-way ligation of a fragment obtained by restricting pCS3 (See para. E.11. below) with EcoRI, SalI followed by BAP treatment and a fragment obtained from pP$_L$MspSA by restriction with EcoRI, SalI and PstI. (see FIG. 3). The ligation mixture was then used to transform MC1000-39351 and transformants selected by Amp$^R$. The correct construction of the desired plasmid pP$_L$OPMspSA was confirmed by restriction analysis and Maxam-Gilbert sequencing.

The colonies transformed with each of the foregoing plasmids were grown at 30° C. in TYE medium containing 100 μg/ml ampicillin, and at the end of log phase the temperature raised to 42° C. After 1.5 hr the cells were centrifuged and sonicated and the sonicate assayed by the assay of Chung, D. W., et al, *Infect Immun* (1977) 16: 832 for enzymatic activity. Activity corresponding to DTA-B'-spacer at levels of 1–10 μg/ml medium was found when pP$_L$MspSA was used and 20–150 μg/ml when pP$_L$OPMspSA was used. Production of the desired DT A-B' spacer was confirmed by Western Blot.

In a similar manner, expression vectors were constructed for DT-A-B'-Cys, an analogous cytotoxic portion containing a C-terminal cysteine. Details of this construction are disclosed in copending Ser. No. 578,122, filed 8 Feb. 1984, assigned to the same assignee and incorporated herein by reference. This vector, denoted there $pP_L$OPMspCys, was used to transform *E. coli* MC1000, and production of the DT-A-B'-Cys protein confirmed by Western Blot.

E.7. Isolation of DT-A-B'-spacer

To produce sufficient protein for isolation, cultures of *E. coli* MC1000 transformed with, respectively, $pP_L$OPMspRT (which encodes the DT-A-B' fragment alone; see Ser. No. 578,122, supra) $pP_L$OPMspCys, and $pP_L$OPMspSA were grown in fermenters on minimal media supplemented with casamino acids and ampicillin using glucose as carbon source. Each fermenter was inoculated from a seed grown at 30° C. to an initial dry weight of 0.5 mg/l. When the $OD_{680}$ reached 2–4, the temperature was rapidly shifted from 30° to 43° C., and growth continued for an additional 5 hrs. The cells were harvested and stored at −70° C. Analysis by SDS-PAGE showed estimates for yields of the desired proteins in the range of 500–1000 mg/l culture.

E.7.a. DT-A-B' Peptide Purification

10–20 g cells were resuspended in 20 ml 50 mM Tris, 1 mM EDTA, pH 8.2 and sonicated. Following centrifugation, the supernatant was diluted approximately 5 fold in 5 mM Na phosphate, pH 6.8, 0.5M NaCl and applied to a phenylsepharose column. The desired peptide eluted in approximately 5 mM Na phosphate, pH 6.8, giving a fraction of greater than 80% purity.

E.7.b. DT-A-B'-Cys Peptide

A similar procedure attempted on the cells harboring $pP_L$OPMspCys did not result in any soluble peptide. The desired peptide remained with the pelleted cells during centrifugation, and was not recoverable in the supernatant.

E.7.c. DT-A-B'-spacer

Sixteen grams of cells transformed with $pP_L$OPMspSA were resuspended in 20 ml 50 mM Tris, pH 8.2, 1 mM EDTA, 10 mM DDT and sonicated. The supernatant from centrifugation was diluted 5–10 fold in 5 mM Na phosphate, pH 6.8, 10 mM DTT and applied to a DEAE Sephacel column. The protein was eluted using a 0-300 mM NaCl gradient and 5 mM Na phosphate, pH 6.8, 10 mM DTT. The fractions containing the desired peptide were pooled, dialyzed against 5 mM Na phosphate, pH 6.8, 10 mM DTT and loaded onto an NAD-Agarose (P.L. Biochemical TYPE1) column. Following elution using a 0-1M NaCl gradient in the same buffer, desired fractions were pooled, concentrated, and run over a Sephacryl S-200 sizing column and the resulting fractions estimated to be 80% pure.

E.8. Assay for Cytotoxicity

The DT-A-B'-spacer was conjugated with antibreast monoclonal antibody 260F9, (hybridoma deposited at the ATCC on 27 Jan. 1984 under accession number HB8488 and described in commonly owned copending Ser. No. 577,976, filed 8 Feb. 1984) and the conjugates assayed for immunotoxicity. Controls utilized reduced ricin toxin A chain (RTA) or diphtheria toxin A chain (DTA) which, therefore, contain free sulfhydryl groups for analogous conjugation with the antibody.

E.8.a. Conjugation of Cytotoxic Portion to Antibody

To form the conjugate, breast monoclonal antibody 260F9 or other antibodies as specified below were first derivatized with SPDP or

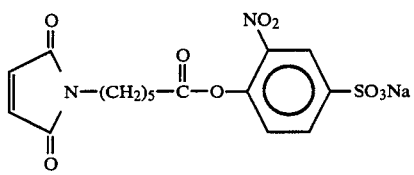

(mal-sac-HNSA). The antibodies derivatized to SPDP were used to form disulfide links to the free cysteine sulfhydryls of DT-A-B'-spacer, DTA or RTA. Those derivatized with mal-sac-HNSA were used to form thioether linkages with DT-A-B'-spacer.

For SPDP, a 10-20 fold molar excess of SPDP was added to a solution containing 20 mg/ml of antibody in PBS and incubated at room temperature for 1 hr, and then dialyzed against PBS to remove unreacted SPDP. It was calculated that approximately 2-5 pyridyl-disulfide moieties were introduced into each antibody using this procedure.

To complete the conjugation with SPDP to give a disulfide linkage to the cytotoxic portions, DT-A-B'-spacer solution or solution of RTA or DTA containing 1-2 mg/ml which had been stored in reducing agent in 4° C. was passed over a Sephadex G-25 column equilibrated in PBS to remove the reducing agent, and the DT-A-B'-spacer or other cytotoxic portion was mixed with derivatized antibody in 2-4 molar excess cytotoxic portion. Conjugation was confirmed by spectrophotometric determination of released pyridine-2-thiol and by SDS-PAGE.

For mal-sac-HNSA, approximately 0.2 ml of mal-sac-HNSA solution containing 1 mg/ml was added to 1 ml antibody solution containing 3-8 mg/ml in PBS. The mixture was kept at room temperature and monitored until 5 mal-sac-HNSA moieties were incorporated per antibody. The reaction was then stopped by desalting the mixture on a G-25 column equilibrated in 0.1M Na phosphate, pH 6.

The DT-A-B'-spacer, stored in reducing agent at 4° C., was passed over PBS-equilibiated Sephadex G-25 to remove reducing agent, and the protein (1-2 mg/ml) mixed in 2-4 molar excess with the derivatized antibody. Conjugation was confirmed by SDS-PAGE.

E.8.b. Assay

In a typical protocol, breast tumor cells (MCF-7) were seeded in 8 ml glass vials and dilutions of the immunoconjugates were added. Following incubation for 22 hr at 37° C., the medium was removed and replaced with medium containing $35_S$ methionine. Following a 2-hr pulse, the medium was aspirated, the monolayer was washed twice with 10% trichloroacetic acid containing 1 mg/ml methionine and the vials were dried. Following the addition of 3 ml of 4ad scintillation fluid containing 20% (v/v) Triton X-100, the vials were counted. Toxicity was expressed as the concentration of protein required to inhibit protein synthesis by 50% ($TCID_{50}$).

The results of these assays are shown in Table 1 both for 260F9, and other antibody partners.

TABLE 1

| Monoclonal Antibody | Ab—DTA | $TCID_{50\%}$ (nM) Ab—DT—A—B'—spacer | Ab—RTA |
|---|---|---|---|
| ATR[1] | 10 | 2 | 0.1 |
| 260F9 | 30 | 0.3 | 0.1 |
| 106A10 | >100 | 7 | 1 |
| 208D11[2] | >100 | 40 | 4 |
| 245E7[3] | >100 | 50-100 | 10 |
| MOPC21[4] | >100 | >100 | >100 |

[1]positive control, anti-transferrin receptor antibody
[2]hybridoma deposited 1/27/84 at ATCC, number HB8487, described in U.S. Ser. No. 577,976
[3]hybridoma deposited 1/27/84 at ATCC, number HB8489, described in U.S. Ser. No. 577,976
[4]negative control, purchased from Zymed Labs The foregoing assay was run as set forth above, but substituting alternate cell lines for MCF-7. The results are shown in Table 2.

TABLE 2

| | RTA | $TCID_{50\%}$ (nM) DT—A—B'—spacer | |
|---|---|---|---|
| Cell Line | Disulfide | Disulfide | Thioether |
| MCF—7 | 0.1 | 0.3 | ND |
| CAMA—1 | 0.4 | 1.0 | 0.5 |
| BT—20 | 9 | 1.6 | 1.4 |
| SKBR3 | 0.06 | 0.6 | 0.2 |
| CC95 | >100 | >100 | ND |

The cell lines shown, CAMA-1, BT-20, and SKBR-3 are other breast tumor cell lines; a normal fibroblast cell line CC-95 was also used. The DT-A-B'-spacer was comparably active with respect to the alternative breast tumor lines, but relatively inactive against the normal cells.

E.9 Construction of Plasmids with a Portable $P_L N_{RBS}$ EcoR 1-Hind III Cassette Three plasmids were constructed which can serve as sources for the EcoRI (or PstI)-HindIII $P_L N_{RBS}$ cassette: pFC5, $pP_L 322$, and $pP_L Kan$.

For each of these plasmids, the DNA sequence containing $P_L$ λ phage promoter and the ribosome binding site for the N-gene ($N_{RBS}$) is obtained from a derivative of pKC30 described by Shimatake and Rosenberg, Nature (1981) 292: 128. pKC30 contains a 2.34 kb fragment from λ phage cloned into the HindIII-BamHI vector fragment from pBR322. The $P_L$ promoter and $N_{RBS}$ occupy a segment in pKC30 between a BglII and HpaI site.

The BglII site immediately preceding the $P_L$ promoter was converted into an EcoRI site as follows: pKC30 was digested with BglII, repaired with Klenow and dNTPs, and ligated with T4 ligase to an EcoRI linker (available from New England Biolabs) and transformed into *E. coli* MM294. Plasmids were isolated from $Amp^R Tet^S$ transformants and the desired sequence confirmed by restriction analysis and sequencing. The resulting plasmid, pFC3, was double-digested with PvuI and HpaI to obtain an approximately 540 bp fragment framing the desired sequence. This fragment was partially digested with HinfI and the 424 bp fragment isolated and treated with Klenow and dATP, followed by S1 nuclease, to generate a blunt-ended fragment with 3' terminal sequence -AGGAGAA where the -AGGAGA portion is the $N_{RBS}$. This fragment was restricted with EcoR 1 to give a 347 base pair DNA fragment with 5'-EcoRI/Hinf(partial repair S1 blunt)-3' termini.

To obtain plasmids containing desired EcoRI/HindIII cassette containing $P_L N_{RBS}$, the resulting fragment was ligated into an EcoRI/HindIII (repaired) cleaved plasmid vector fragment obtained from one of three such host plasmids: pβ1-Z15, pBR322, and pDG144.

pβ1-Z15, deposited Jan. 13, 1984 1983 ATCC No. 39578, was prepared by fusing a sequence containing ATG plus 140 bp of β1-IFN fused to lac Z into pBR322. In pβ1-Z15 the EcoRI site of pBR322 is retained, and the insert contains a HindIII site immediately preceding the ATG start codon. pβ1-Z15 was restricted with HindIII, repaired with Klenow and dNTP, and then digested with EcoRI. The resulting EcoRI/HindIII (repaired) vector fragment was ligated with the EcoRI/HinfI (repaired) fragment above. The ligation mixture was used to transform MC1000-39351 and transformants containing the successful construction were identified by ability to grow on lactose minimal plates at 34° but not at 30%. (Transformants were plated on X-gal Amp plates at 30° and 34° and minimal-lactose plates at 30° and 34°. Transformants with the proper construction are blue on X-gal-Amp plates at both temperatures, but grow on minimal lactose plates only at 34°.) The successful construct was designated pFC5.

In the alternative, pBR322 may also be used as the cloning vector to carry the desired EcoRI/HindIII $P_L N_{RBS}$ cassette. pBR322 was digested with HindII, repaired with Klenow and dNTPs, and then further digested with EcoRI. The vector fragment was then ligated to the EcoRI/HinfI (repaired) fragment prepared above. The ligation mixture was then transformed into MM1000-39351, and successful transformants identified by $Amp^R Tet^S$. Plasmids were isolated from successful transformants and a successful ligation confirmed by sequencing, and designated $pP_L 322$.

The third host plasmid vector to obtain and provide the cassette was pDG144, deposited Jan. 13, 1984 ATCC No. 39579. pDG144 is extensively described in another application and does not constitute a part of the herein invention. It is an altered pBR322 containing an intact $Amp^R$ gene, and a coding sequence for a protein conferring resistance to kanamycin ($Kan^R$) preceding a synthetic polylinker. The polylinker sequence immediately preceding the ATG start codon for the kanamycin gene can be removed by digesting with EcoRI and HindIII and $P_L N_{RBS}$ inserted.

Accordingly, pDG144 was digested with HindIII, blunt-ended with Klenow and dNTPs, and then digested with EcoRI. The vector fragment was ligated with the above-prepared EcoRI/HinfI (repaired) fragment and transformed into MC1000-39351 $Amp^R Kan^R$ colonies were selected and plasmids isolated and the correct construction verified by restriction analysis and sequencing. One plasmid containing the correct sequence was designated $pP_L Kan$.

Each of the above resulting vectors, pFC5, $pP_L 322$, and $pP_L Kan$, may be used to clone and provide the EcoRI/HindIII $P_L N_{RBS}$ cassette. The cassette can then conveniently be placed behind an ATG start codon having a HindIII site immediately preceding it.

E.10 Construction of pTrpSmlMbo pTrpSmlMbo contains the DT-A fragment coding sequence followed by the Mbo terminator sequence (supra) under the control of the trp promoter. The construction is from pTS12 (a plasmid containing the DT-A and Mbo terminator) and pDG141, which contains the trp promoter (see FIG. 4).

pTS12 (53.5 μg) was restricted with HhaI blunt-ended with Klenow, 18 μg of the resulting fragments ligated to 3.15 nmoles of the oligomeric linker CCCCGGGG, and then treated with SmaI. The resulting sequence at the 5' terminus was thus modified to give the sequence GGGGCTGA which encodes the peptide sequence beginning with amino acid 1 of the DT-A fragment, (See FIG. 5). The 3' end of the ligation product terminates in the first HhaI site of pBR322 following the SalI site, and the fragment contains the entire coding sequence along with in reading frame with terminator for the small Mbo fragment. The desired 654 bp fragment was isolated using 6% PAGE, and elution by crush and soak.

One picomole of this modified prepared fragment was ligated with 0.7 μg of pDG141 which had been restricted with SacI, blunt-ended with Klenow, and BAPed (the preparation of pDG141 is described below). The pDG141 derived fragment has an ATG start codon operably linked to the trp promoter. The resulting ligation mixture was transformed into *E. coli* MM294, and resistant colonies grown in 10 ml TYE' medium containing 10 μg/ml ampicillin and screened for plasmid size. Those colonies which contained plasmids larger than pDG141 were screened for expression of the DT-A fragment.

The cells were grown to log phase in 10 ml of the TYE'-Amp 100 medium at 37° for 4 hr. To demonstrate expression, one ml of the culture was centrifuged and the pellet resuspended in 20 μl buffer containing 625 mM Tris, pH 6.8, 3% SDS. After heating at 95° C. for 5 min, samples were run in 12.5% SDS-PAGE with a 3% stacking (Laemmli, et al, *Nature* (1970) 227: 680). Two clones which showed an additional protein band at the expected molecule weight were confirmed by the EF-2 ADP-ribosylation assay according to the procedure of Chung, D. W., et al, *Infect Immun* (1977) 16: 832. These colonies, designated ptrpSmlMbo, produced 20 μg of DT-A per ml of culture. The antigenicity and molecular weight of the product were confirmed by Western Blot.

E.10.a Preparation of pDG141 pDG141, deposited 24 Jan., 1984, ATCC No. 39588, contains the trp control sequences immediately upstream from an ATG start codon. The sequence downstream of the ATG provides a SacI cleavage site which cuts between the G and the succeeding bp. Thus this plasmid contains a trp control sequence-ATP cassette excisable by digestion with PstI or EcoRI and SacI. pBR322-Trp3 is used to provide a trp (PstI/HindIII repaired) cassette containing the promoter and RBS. pBW20 is used to provide an ATG start codon followed by a SacI site.

pBR322-Trp3 (12 ng) restricted with PstI, and HindIII was ligated with 1.34 ng of similarly restricted pBW20. The ligation mixture was subsequently digested with BamHI to linearize any ligation products which contained the HindIII/PstI unwanted vector fragment from pBR322-Trp3. The ligation mixture was used to transform E. coli MM294, and the desired colonies selected using L broth medium containing 50 μ/ml ampicillin on plates pre-spread with 500 mg tryptophan. Correct construction was confirmed by sequencing.

E.10.a.1. Construction of pBR322-trp pBR322-trp has the trp promoter/operator/ribosome binding site sequence absent the attenuator region, and was obtained from pVH53 a plasmid obtained from C. Yanofsky, Stanford University. A number of other plasmids containing these control sequences are available as is known in the art.

pVH153 was treated with HhaI (which cuts leaving an exposed 3' sticky end just 5' of the trp promoter) blunt ended with Klenow, and partially digested with TacI. The 99 bp fragment corresponding to restriction at the TacI site immediately preceding the ATG start codon of trp leader was isolated, and then ligated into EcoRI/ClaI digested, BAPed pBR322 to provide pBR322-Trp3. The HindIII site immediately downstream from the pBR322 ClaI site permits excission of the desired trp fragment as an EcoRI/HindIII cassette.

E.10.a.2. The Construction of pBW20 pBW20 is a HindIII (repaired)/PvuII digest of pBR322 containing an insert of the double-stranded dodecamer: TATGAGCTCATA. This insert was made by ligating the blunt-ended fragments, transforming competent E. coli MM294, and selecting Amp$^R$Tet$^S$ colonies of appropriate construction as confirmed by sequencing. The sequence resulting in the region of the insert is as follows:

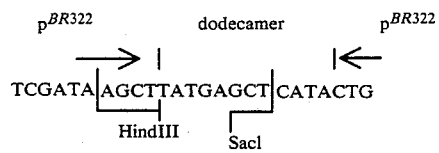

E.10.b. pTS12

The oligonucleotide

---
GA TCT GTT GGC TCG AGT TGA
Arg Ser Val Gly Ser Ser Term
--- which encodes the amino acid sequence subsequent to the Mbo cleavage site for six additional amino acids prior to a termination codon was synthesized using the triester method of Matteucci, et al (supra); kinased and hybridized to the complementary synthetic fragment to give ---
5' HO GATCTGTTGGCTCGAGTTGA
            ACAACCGAGCTCAACTAGCT P
  BglII                SalI
---

One pmole of the double-stranded oligonucleotide was then placed in a three way ligation mixture with 1.4 pmoles (0.8 μg) of Mbo fragment 1 and the vector fragment formed from 1 μg pBR322 which had been treated with BamHI, SalI and BAP. The mixture was ligated overnight before transforming into E. coli MM294. Amp$^R$Tet$^S$ colonies were selected and the desired construction confirmed by DNA isolation, restriction analysis and sequencing. The correct plasmid was desingated pTS12.

E.11 Construction of pCS3 pCS3 is constructed from pOP9, a high copy number derivative of pOP6 (Gelfand, D., et al, Proc Natl Acad Sci (USA) (1978)75: 5869), with a temperature sensitive fragment from pEW27 which is described by E. M. Wong, Proc Natl Acad Sci (USA) (1982) 79: 3570. The EcoRI/PvuII shorter fragment from pEW27 contains mutations in the region surrounding the origin of replication such that replication is inhibited at lower temperatures but increased at high ones.

To construct to pCS3, pOP6 was first modified through several steps: 50 μg of pOP6 was digested to completion with 20 units each of BamHI and SstI. In order to eliminate the SstI 3' protruding ends and filling the BamHI 5' ends, the digested pOP6 DNA was treated with E. coli DNA polymerase I (Klenow) in a two-stage reaction, first, at 20° C. for elimination of the SstI protruding end and then at 0° C. for repair at the 5' end. This blunt-ended fragment was ligated and 0.02 picomoles used to transform competent DG75 (O'Farrell, P., et al, J Bacteriol (1978) 134: 645). Transformants were selected on L plates containing a 50 μg/ml ampicillin and screened for a 3.3 kb deletion, loss of an Sst restriction endonuclease site, and presence of a newly formed BamHI site.

One candidate, designated pOP7 was chosen and BamHI site deleted by digesting 25 μg of pOP7 with 20 units BamHI and religating with T4 DNA ligase. Competent DG75 was treated with 0.1 μg of the ligation mixture DNA, and transformants selected on plates containing 50 μg/ml ampicillin. Candidates were screened for loss of the BamHI restriction site.

pOP8 was selected and modified to result in pOP9. The AvaI (repaired)/EcoRI Tet$^R$ fragment from pBR322 was isolated and ligated to the isolated PvuII (partial)/EcoRI 3560 bp fragment from pOP8. Ligation of the 1.42 kb EcoRI/AvaI (repaired) Tet$^R$ (fragment A) and the 3.56 kb EcoRI/PvuII Amp$^R$ (fragment B) used 0.5 μg of fragment B and 4.5 μg fragment A in a two-stage reaction in order to favor intermolecular ligation of the EcoRI ends. Competent DG75 was transformed with 5 μl of the ligation mixture, and transformants selected on ampicillin 50 μg/ml or ampicillin or tetracycline (15 μg/ml). pOP9 isolated from Amp$^R$Tet$^R$ transformants showed a high copy number, colicin resistance single restriction sites for EcoRI, BamHI, PvuII and HindIII; two restriction sites for HincII, and the appropriate size and HaeIII digestion pattern.

50 μg pEW27 DNA was digested to completion with PvuII and EcoRI. Similarly, 50 μg of pOP9 was digested to completion with PvuII and EcoRI and the 3.3 kB fragment isolated.

0.36 μg (0.327 picomoles) pEW27 fragment and 0.35 μg (0.16 picomoles) pOP9 fragment were ligated and used to transform *E. coli* MM294. Ampicillin-tetracycline resistant transformants were selected. Successful colonies were screened at 30° C. and 40° C. on beta lactamase assay plates and then for plasmid DNA levels following growth at 30° C. and 41° C. Plasmids isolated from a colony showing improved amp$^R$ and incresed plasmid DNA levels at the higher temperature were confirmed by restriction analysis and designated pCS3.

We claim:

1. A recombinant polypeptide, useful in making toxin conjugates, comprising:
    a diptheria toxin, or an enzymatic fragment of diptheria toxin;
    and a spacer covalently linked to said diptheria toxin comprising an amino acid sequence which has the formula:

Gly-Thr-Gly-Ser-Gly-(Pro)$_6$-Ser-Gly-Ser-Gly-Thr-Cys.

2. A conjugated toxin comprising the recombinant polypeptide of claim 1 covalently linked to a binding moiety wherein said binding moiety is covalently linked to said spacer amino acid sequence and comprises an antibody or fragment thereof which is capable of binding to an antigenic determinant.

3. A method of killing undesirable cells in mammals comprising administering to a mammal in need of such treatment an effective amount of a conjugated toxin comprising; an antibody or fragment thereof which binds to a target cell which comprises the corresponding antigenic determinant; and a recombinant protein comprising:
    a spacer covalently bound to said antibody or fragment thereof comprising an amino acid sequence which has the formula:

Gly-Thr-Gly-Ser-Gly-(Pro)$_6$-Ser-Gly-Ser-Gly-Thr-Cys;

and a cytotoxic protein fragment covalently bound to said spacer selected from the group consisting of diptheria toxin and enzymatically active fragments of diptheria toxin.

* * * * *